(12) United States Patent
Baranton et al.

(10) Patent No.: US 8,708,490 B2
(45) Date of Patent: Apr. 29, 2014

(54) METHOD AND A DEVICE FOR AUTOMATICALLY MEASURING AT LEAST ONE REFRACTIVE CHARACTERISTIC OF BOTH EYES OF AN INDIVIDUAL

(75) Inventors: Konogan Baranton, Charenton-le-Pont (FR); Bjorn Drobe, Charenton-le-Pont (FR)

(73) Assignee: Essilor International (Compagnie Generale d'Optique), Charenton le Pont (FR)

( * ) Notice: Subject to any disclaimer, the term of this patent is extended or adjusted under 35 U.S.C. 154(b) by 139 days.

(21) Appl. No.: 13/508,563

(22) PCT Filed: Nov. 9, 2010

(86) PCT No.: PCT/FR2010/000747
§ 371 (c)(1),
(2), (4) Date: May 8, 2012

(87) PCT Pub. No.: WO2011/058244
PCT Pub. Date: May 19, 2011

(65) Prior Publication Data
US 2012/0274902 A1  Nov. 1, 2012

(30) Foreign Application Priority Data
Nov. 13, 2009  (FR) ...................................... 09 05467

(51) Int. Cl.
*A61B 3/14* (2006.01)
*A61B 3/02* (2006.01)
*H04N 7/18* (2006.01)

(52) U.S. Cl.
USPC .............................. 351/206; 351/243; 348/78

(58) Field of Classification Search
USPC ......... 351/200, 203–206, 208–210, 221–222, 351/243–246, 159; 348/78
See application file for complete search history.

(56) References Cited

U.S. PATENT DOCUMENTS

| 4,834,528 | A |   | 5/1989  | Howlan et al. |
| 5,583,798 | A | * | 12/1996 | Franz et al. .................... 702/127 |

(Continued)

FOREIGN PATENT DOCUMENTS

| DE | 197 19 694   | 11/1998 |
| WO | 2008/132356  | 11/2008 |

OTHER PUBLICATIONS

International Search Report dated Feb. 4, 2011, corresponding to PCT/FR2010/000747.

*Primary Examiner* — Thomas K Pham
*Assistant Examiner* — Brandi Thomas
(74) *Attorney, Agent, or Firm* — Young & Thompson (57) ABSTRACT

A method for automatically measuring at least one refractive characteristic of both eyes of a person, includes: a) adjusting at least one position of a person's head, in a reference system connected to an image capture apparatus set up to convert each captured image into a signal representing the image; b) illuminating both eyes with at least one light source, whose position is known within the reference system; c) measuring at least one sight direction parameter connected to the sight direction of the person within a reference system connected to the head thereof; d) capturing at least one retinal reflection image from the light source onto the retina of both eyes; f) determining, from the captured image in Step d), the refractive characteristic of the eyes; and h) storing the sight direction parameter in relation to the predetermined refractive characteristic during the image capture in Step c).

33 Claims, 3 Drawing Sheets

(56) References Cited

U.S. PATENT DOCUMENTS

| | | |
|---|---|---|
| 6,616,277 B1 | 9/2003 | Davenport |
| 6,663,242 B1 | 12/2003 | Davenport |
| 7,341,346 B2 * | 3/2008 | Hanaki et al. ............... 351/205 |
| 7,747,068 B1 * | 6/2010 | Smyth et al. ............... 382/154 |
| 2003/0108350 A1 | 6/2003 | Brauning |
| 2003/0169907 A1 | 9/2003 | Edwards et al. |
| 2009/0079937 A1 | 3/2009 | Chen |
| 2010/0013966 A1 | 1/2010 | Feng et al. |

* cited by examiner

METHOD AND A DEVICE FOR AUTOMATICALLY MEASURING AT LEAST ONE REFRACTIVE CHARACTERISTIC OF BOTH EYES OF AN INDIVIDUAL

TECHNICAL FIELD TO WHICH THE INVENTION RELATES

The present invention relates in general to a method of measuring optical characteristics of an individual's eyes. More particularly, it relates to a method of automatically measuring at least one refractive characteristic of both eyes of an individual.

The invention also relates to a measuring device that enables such a method to be implemented.

TECHNOLOGICAL BACKGROUND

The refractive characteristics of an individual's eyes are magnitudes that play an essential role in preparing a pair of eyeglasses for correcting that individual's vision.

Various methods and devices are presently known for determining the refractive characteristics of an eye of an individual. They are based in particular on the photorefraction technique and on a so-called "skiascopy" technique.

Nevertheless, those methods and the associated devices are time-consuming to implement.

The manual devices with which an observer observes said retinal reflection with the naked eye are not very accurate. Accuracy is improved by using a detector, but the measurements take a long time to perform, since each of the individual's eyes needs to be measured individually: only the retinal reflection from only one of the two eyes of the individual is observed at any one time.

In addition, known devices include constraining means for imposing a predetermined posture on the head and/or the eyes of the individual in a frame of reference associated with the image capture device, e.g. by means of a rest for the forehead and by means of a chin support, and/or means for constraining the gaze direction, e.g. by having a target for the individual to gaze at.

The measurements of refractive characteristics performed using such existing methods and devices are therefore not performed under natural conditions concerning the posture and the gaze direction of the individual, and therefore do not enable the individual's binocular vision to be taken into account.

For example, those measurements do not make it possible to determine the refractive characteristics of an individual's eye under near or intermediate vision conditions.

Unfortunately, the refractive characteristics of an eye may change significantly depending on vision conditions, on the task to be performed by the individual, and on the individual's posture and gaze direction.

OBJECT OF THE INVENTION

An object of the present invention is to provide a method and a device making it possible to measure the refractive characteristics of both eyes of an individual in a manner that is rapid and reliable, while the individual is in a non-constrained, comfortable, and natural posture, and under determined vision conditions. This natural posture corresponds to the posture that is the most ergonomic and the least tiring for the individual. In other words, it corresponds to the posture that is usually taken up by the individual.

To this end, the invention provides a method of automatically measuring at least one refractive characteristic of both eyes of an individual, the method comprising the following steps:

a) illuminating both eyes by means of at least one light source of known position in a frame of reference associated with an image capture device adapted to convert each captured image into a signal that is representative thereof;

b) adjusting at least one posture of the individual's head in accordance with the wishes of said individual and in this frame of reference associated with the image capture device;

c) measuring at least one gaze direction parameter associated with the gaze direction of the individual in a frame of reference associated with the individual's head;

d) using said image capture device to capture at least one image of the retinal reflection of said light source on the retinas of both eyes of the individual;

f) from said at least one image captured in step d), determining said refractive characteristic for each of the eyes of the individual; and h) storing the gaze direction parameter associated with the gaze direction of the individual as measured during the image capture of step d) in association with the determined refractive characteristic.

The invention also provides a method of automatically measuring at least one refractive characteristic of both eyes of an individual under predefined vision conditions, the method comprising the following steps:

a) adjusting at least one posture of the individual's head in accordance with the wishes of said individual, in a frame of reference associated with an image capture device adapted to convert each captured image into a signal that is representative thereof;

b) illuminating both eyes by means of at least one light source of known position in said frame of reference associated with the image capture device;

c) measuring at least one gaze direction parameter associated with the gaze direction of the individual in a frame of reference associated with the individual's head;

i) capturing by means of said image capture device at least one image of the retinal reflection of said light source on the retinas of both eyes of the individual, the image being captured in an image capture plane and for a value of said gaze direction parameter that is situated in a range corresponding to said predefined vision conditions; and j) determining from said at least one captured image, said refractive characteristic of each of the eyes of the individual in said predefined vision conditions.

Thus, the refractive characteristic of each of the eyes of the individual, e.g. the sign of the ametropia or the value of said ametropia, i.e. the spherical and/or cylindrical powers thereof, is measured in a posture that is natural and comfortable for the individual, thereby enabling said refractive characteristic to be determined under real vision conditions of the individual. This improves the accuracy of these measurements. Furthermore, this refractive characteristic is associated with a gaze direction parameter linked to the individual's gaze direction.

The term "linked to the gaze direction" is used to mean that there exists a mathematical relationship between said gaze direction parameter and said gaze direction of the individual that enables either one to be calculated from the other.

The link may be direct, with the gaze direction parameter then typically consisting in using image recognition to track the orientation of the eyes, or else indirect, the measured parameter then relating exclusively to the head and consisting in one or more position and/or orientation coordinates of the head. This is described in greater detail below in a particular implementation of the invention.

The method thus enables a map to be established associating each determined value of the refractive characteristic of the eyes to be associated with a corresponding gaze direction of the individual. This makes it possible in particular to distinguish between refractive characteristic values that are associated with near vision or intermediate vision from those associated with far vision.

The term "near vision" is used herein to mean conditions in which the individual gazes on an item that is 25 centimeters (cm) to 69 cm away, the term "intermediate vision" is used to designate conditions in which the individual is gazing on an item that is 70 cm to 199 cm away, and the term "far vision" is used to designate conditions in which the individual is gazing at an item that is distant by at least 200 cm.

The individual adjusts the position and the orientation of the image capture device either manually or by remote control or by giving instructions for the adjustments to be made as the individual wishes.

Alternatively, if the position of the image capture device is stationary, the individual takes up a posture as desired by that individual while facing the device.

In this method, the refractive characteristics of both eyes of the individual are measured simultaneously. Measurement is thus simple and can be implemented quickly. The method also makes it possible to take account of the reality of the accommodation system and of the convergence of the eyes in binocular vision.

According to a first advantageous characteristic of the invention, the following step is also provided:

e) determining from said at least one captured image a width or a luminance distribution of the image of the retinal reflection of the light source, and determining said refractive characteristic of each of the individual's eyes as a function of said width or said luminance distribution.

Under such circumstances, advantageously, both eyes are illuminated simultaneously, and the images of the retinal reflections of the light source on the retinas of both eyes are captured simultaneously, and in step e), the width or the luminance distribution of the image of the retinal reflection of the light source is determined at least from said signals relating to the retinal reflections of both eyes as captured simultaneously in each posture of the individual's head relative to said light source.

This embodiment of the invention advantageously makes it possible to determine said refractive characteristic by a photorefraction method.

According to another advantageous characteristic of the invention, both eyes are illuminated simultaneously, and the images of the retinal reflections of the light source on the retinas of both eyes are captured simultaneously, and in step e), the width or the luminance distribution of the image of the retinal reflection of the light source is determined at least from said signals relating to the retinal reflections of both eyes as captured simultaneously in each posture of the individual's head relative to said light source.

Thereafter, a value is deduced for the ametropia of each of the individual's eyes from the width or from the luminance distribution of the image of the retinal reflection of the light source.

This makes it possible to determine an accurate value for the ametropia of each of the eyes.

According to another advantageous characteristic of the invention, at least two images are captured of the retinal reflections of said light source on the retina of each of the individual's two eyes, and the method further includes the following step:

e') determining from said at least two captured images a movement of the image of the retinal reflection of the light source;

said refractive characteristic of each of the individual's eyes being determined as a function of said movement.

According to another advantageous characteristic of the invention:

for the posture of the individual's head relative to said light source differing during the two image captures;

in step c), during said image captures, at least one posture parameter of the individual's head is measured in the frame of reference of the image capture device; and in step e'), the movement of the image of the determined retinal reflection is compared with the difference in posture of the individual's head relative to the light source between the two image captures as a function of said head posture parameter measured in step c);

said refractive characteristic of each of the individual's eyes being deduced from the comparison.

This implementation of the invention advantageously makes it possible to determine said refractive characteristic by a skiascopy method.

Then, advantageously, the sign of the ametropia of each of the individual's eyes is deduced from said comparison.

According to another advantageous characteristic of the invention, both eyes are illuminated simultaneously, and the images of the retinal reflections of the light source on the retinas of both eyes are captured simultaneously, and wherein, in step e'), the movements of the images of the retinal reflections of the light source are determined at least from said signals relating to the retinal reflections of both eyes as captured simultaneously in each posture of the individual's head relative to said light source.

At least one of the following posture parameters of the head is advantageously measured:

a distance between the head or one of the individual's eyes and the image capture device;

a vertical distance between a pupil of the image capture device and an anatomical plane of the individual that is inclined when the individual is in a natural posture and is looking towards the image capture device, said plane corresponding to a horizon anatomical plane that is substantially horizontal when the individual is in a natural posture and looking at the horizon;

a distance between a pupil of the image capture device and the horizon anatomical plane that is substantially horizontal when the individual is in a natural posture and looking at the horizon;

a first angle of inclination of the image capture plane relative to a first reference plane perpendicular to the line connecting one of the individual's eyes with the pupil of the image capture device, about a horizontal axis of this first plane of this reference; and a second angle of inclination of the image capture plane relative to said first reference plane about an axis of this first reference plane perpendicular to said horizontal axis.

By way of example, these posture parameters for the individual's head enable the position of the wearer's head to be determined accurately relative to the image capture device, regardless of the way the individual holds the device.

Preferably, during image capture, a support on which said light source and said image capture device are mounted is carried by said individual in the hand. This makes it possible to ensure that the individual is in a position that the individual finds natural and comfortable.

According to another advantageous and non-limiting characteristic of the invention, a verification step is provided before or after the image capture step for verifying that said at least one image is captured while the individual is looking in the vicinity of a pupil of the image capture device, i.e. looking within a determined area in the vicinity of the pupil.

According to another advantageous and non-limiting characteristic of the invention, said gaze direction parameter consists exclusively in a posture parameter of the individual's head as measured while the individual is gazing at the pupil of the image capture device.

According to another advantageous and non-limiting characteristic of the invention, during a preliminary step before capturing at least one image, vision correction equipment is placed on the face of said individual and wherein the signals representing said captured image and/or the refractive characteristic deduced from said signals is corrected as a function of the power and the deflection of the vision correction equipment.

The images captured during the image capture of the method of the invention can then be processed in order to determine other physico-morphological parameters of the individual, such as the height between the bottom edge of the rim of an eyeglass frame and the center of the pupil of each of the individual's eyes.

According to another advantageous and non-limiting characteristic of the invention, in step c), the individual's gaze direction is calculated from the signals representative of the images of the corneal reflections of both eyes.

In addition, a variant of the method of the invention comprises the following steps:

r) before or during the capture of at least one image, displaying an image before the individual's eyes, the image presenting fuzziness corresponding to lowpass filtering by a frequency filter of given cutoff for filtering the spatial frequencies of said image;

t) storing in memory the refractive characteristic as determined in association with the value of the cutoff frequency of the lowpass filter used in step r); and u) reiterating at least steps b), c), d), f), r), and t) or steps b), c), i), j), r), and t) for different cutoff frequencies of the image filter.

This method thus makes it possible for different values of the cutoff frequency of the filter used in step r), and thus for different degrees of fuzziness in the image, to measure a refractive characteristic of the individual's eyes under conditions of viewing the fuzzy image in question.

It is then advantageously possible to determine how the refractive characteristic of the individual's eyes varies with the varying degree of image fuzziness.

It is also possible to characterize the perception of fuzziness by the individual for different degrees of fuzziness in the image and to determine how the perception of fuzziness varies with the varying degree of image fuzziness.

This variant thus enables a psychophysical test to be performed.

According to another variant of the method:
during said image capture step, at least two images are captured in succession, each corresponding to the images of the two retinal reflections of said light source on the retinas of both eyes of the individual; and
from one of said two images, determining said refractive characteristic of one of the two eyes of the individual, and from the other image, determining the refractive characteristic of the other eye of the individual.

The invention also provides a device for automatically measuring at least one refractive characteristic of both eyes of an individual, the device comprising:

a support;

at least one light source mounted on the support in such a manner as to illuminate at least one of the individual's eyes;

at least one image capture device mounted on said support, adapted to capture at least one image of the retinal reflection of said light source on the retina of each eye of the individual and to convert each captured image into a signal that is representative thereof, the postures of the individual's head relative to the light source differing between the two image captures, said light source being of known position in a frame of reference associated with said image capture device;

means for measuring at least one gaze direction parameter associated with the individual's gaze direction in a frame of reference associated with the individual's head; and a computer adapted to respond to the signal representative of said at least one captured image to determine said refractive characteristic of the individual's eyes and to store in memory said at least one gaze direction parameter associated with the gaze direction of the individual in association with the determined refractive characteristic.

According to an advantageous and non-limiting characteristic of the invention, said means for measuring said posture parameter of the individual's head comprise an element for identifying the position of the individual's head and adapted to be mounted on the head or on eyeglasses of the individual, or an ultrasound measuring device, including at least one ultrasound emitter and at least one ultrasound receiver, or a measuring device using electromagnetic sensors.

This measuring device makes it possible to measure the posture parameter of the individual's head remotely, quickly, and accurately.

According to another advantageous and non-limiting characteristic of the invention, the light source comprises a plurality of secondary light sources having positions relative to one another that are known, each of which sources may be switched on independently of the others.

By activating a different light source for each image capture it is possible to ensure that, providing the individual's head does not move, the postures of the individual's head relative to said light source are different during each image capture.

Alternatively, the light source may be movable relative to the image capture device.

DETAILED DESCRIPTION OF IMPLEMENTATIONS

The following description made with reference to the accompanying drawings that are given by way of non-limiting example shows what the invention consists in and how it can be reduced to practice.

Overall, the idea is to measure automatically at least one refractive characteristic of both eyes of an individual in a natural posture, under vision conditions that are known or determined. Thus, a measurement is performed of a parameter relating to the gaze direction corresponding to each captured image so as either to record this gaze direction parameter in association with the corresponding refractive characteristic of the eyes, or else trigger image captures when the measured gaze direction parameter indicates that the individual is in predetermined vision conditions of interest, or else, after a series of images have been captured, to select images captured under vision conditions of interest in order to determine the refractive characteristic of the eyes under those conditions.

Of particular interest are vision conditions in which the individual is viewing in near vision or in intermediate vision. The refractive characteristics of the eye can be significantly modified by the phenomenon known as "accommodation" whereby the eye tracks near or intermediate vision.

In the example described below, this measurement relies on the principle of skiascopy, e.g. as described in the document entitled "Principles of retinoscopy" published by M. Klein in 1944 in The British Journal of Ophthalmology.

Figures 1, 2:
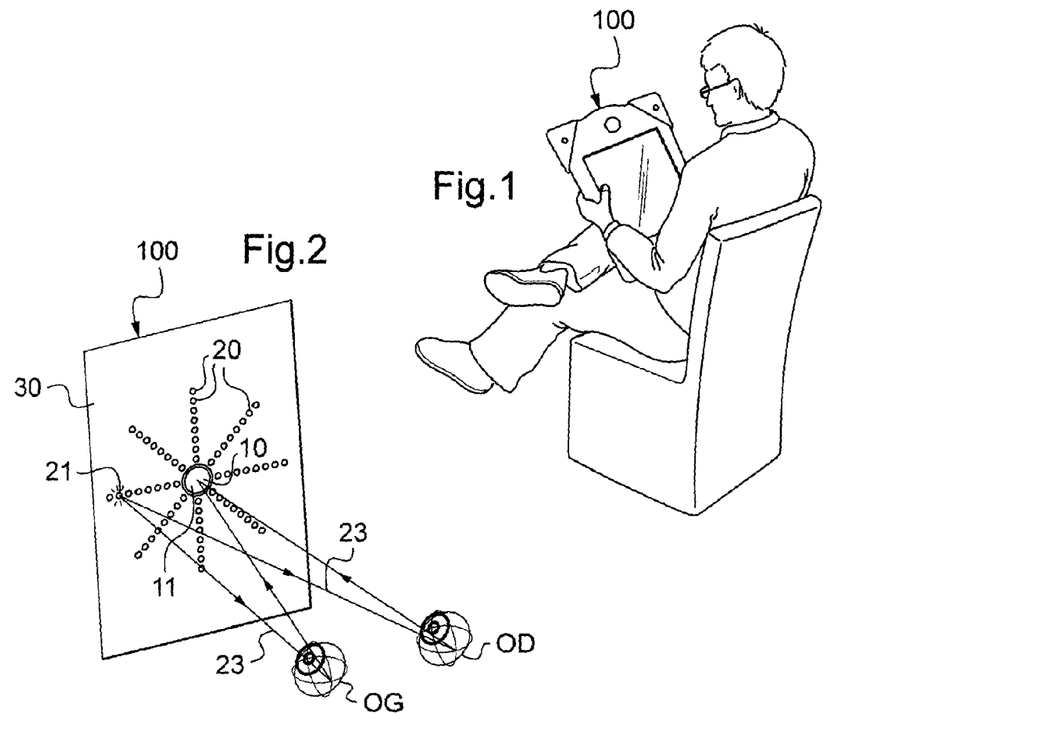
FIG. 1 is a perspective view of an implementation of the method of the invention, in which an individual is holding a measuring device in the hand.
FIG. 2 is a diagrammatic perspective view of the eyes of the FIG. 1 individual when the individual looks towards the FIG. 1 measuring device during a first image capture.
Figures 3, 4:
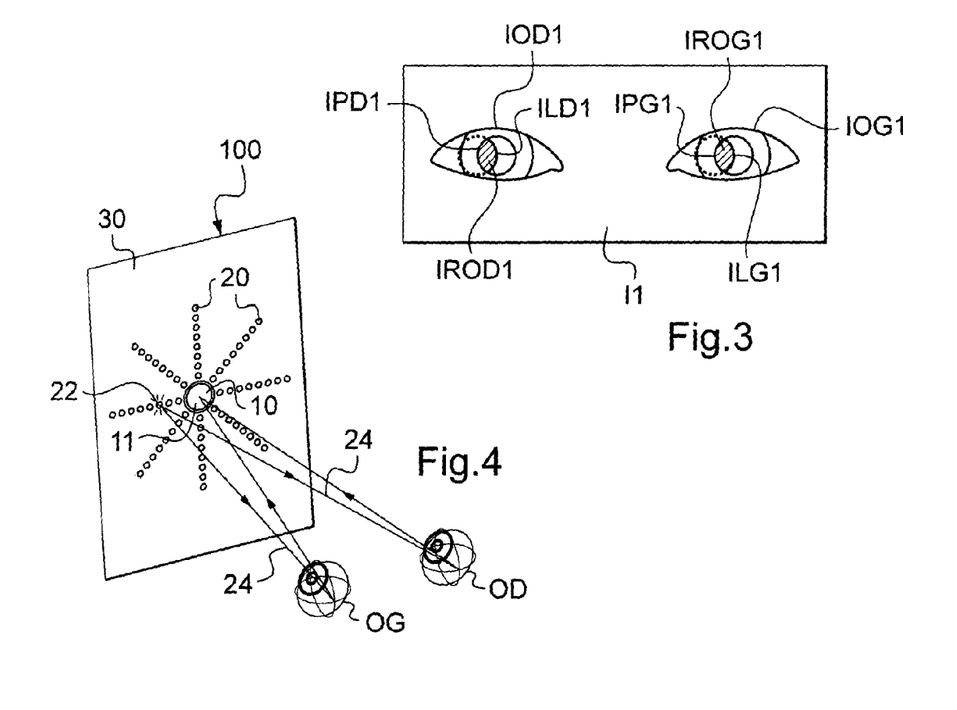
FIG. 3 is a diagrammatic view in the image capture plane of the first image as captured with reference to FIG. 2.
FIG. 4 is a diagrammatic perspective view of the eyes of the FIG. 1 individual while the individual is looking towards the FIG. 1 measuring device during a second image capture.

An example of a measuring device 100 of the invention is shown in FIGS. 1, 2, and 4. The measuring device 100 comprises a housing 30 that is used as a support for an image capture device 10 and for lighting means 20 for lighting the individual's head.

The housing 30 is advantageously in the form of a rectangular tablet.

By way of example, it is desired to determine the objective ametropia of each of the individual's eyes by determining at least one of the following refractive characteristics: ametropia sign; spherical power; cylindrical power; and the position of the axis of the cylinder.

The ametropia sign is negative for myopia and positive for hypermetropia. The value of the ametropia corresponds to the spherical and cylindrical powers of the eye. It is determined along various meridians of the eye. The cylindrical power and the axis of the cylinder characterize the astigmatism of the eye.

These refractive characteristics are essential when selecting optical equipment adapted to the individual, since they enable the type of ophthalmic lens to be determined that is adapted to correcting the individual's ametropia: converging, diverging, or toroidal, and the power of the ophthalmic lens.

The individual is in a natural posture, whether standing or sitting, as shown in FIG. 1. The posture of the individual relative to the measuring device 100 is not constrained by a chin support or a forehead rest. The term "natural" posture is used to mean the posture of the individual that is the most comfortable, the most ergonomic, and the least tiring for the individual.

In a step a), at least one posture of the individual's head is adjusted in a frame of reference associated with the image capture device, depending on the wishes of the individual.

This may simply be performed manually by the individual, taking up a position freely and placing the image capture device 100 where that individual so desires, in particular in a first implementation in which the individual carries the measuring device in the hand, as shown for example in FIG. 1.

In a second implementation in which the image capture device is placed on a support or mounted on a stand, the individual may perform this adjustment remotely by means of a remote control enabling the positioning of the measuring device to be modified, or by giving instructions by voice to an operator who modifies the position of the measuring device depending on the instructions.

Finally, in a third implementation, the measuring device is stationary, and the individual takes up a desired position relative to the measuring device 100.

Whatever the implementation, it is thus possible to capture images of the individual's head in a position that is natural and not constraining. This makes it possible to determine the refractive characteristics of the individual's eyes under real vision conditions.

In a variant, a particular viewing task may be given to the individual, e.g. reading a text placed close to the pupil of the image capture device. This then enables images to be captured and therefore refractive characteristics of the individual's eyes to be determined in the posture that the individual adopts naturally for performing the viewing task.

In a step b), the operator illuminates both of the individual's eyes by means of at least one light source having a known position in a frame of reference (O, X, Y, Z) associated with the image capture device that is known.

The frame of reference (O, X, Y, Z) associated with the image capture device 10 may for example be centered on the pupil of the image capture device. The axes (O, X) (O, Y) extending in the image capture plane PCI, which is the plane of the sensor of the image capture device, here represented by the mean plane of the support 30. The axis (OZ) is the optical axis of the image capture device, which axis is perpendicular to the image capture plane PCI.

In the example shown in FIGS. 1, 2, and 4, the lighting means 20 of the measuring device 100 comprise a plurality of light sources 20. These light sources are preferably of very small size, e.g. almost point-sized. By way of example, each of them represents a width of about 1 millimeter (mm). In this example they are light-emitting diodes (LEDs) 20. Each of these LEDs may be switched on independently of the others and it illuminates both eyes of the individual. The LEDs constitute diverging light sources. They thus advantageously illuminate a very wide solid angle, such that the individual's head is broadly illuminated.

The light sources 20 described herein are primary sources, however in a variant they could be secondary sources obtained by reflecting or deflecting light rays, themselves coming from such primary sources.

In this example, the LEDs are arranged on the front face of the housing 30 that also acts as a support for the image capture device 10, and the position of each of these LEDs in the frame of reference of the image capture device is thus known by construction and is constant.

In this example, the LEDs are located in the plane of the front face of the housing 30, being in alignment along four alignment directions that cross at a point where the pupil 11 of the image capture device 10 is located.

Alternatively, it is possible to envisage using any other type of light source known to the person skilled in the art. In position, it is possible to use a single light source capable of being moved relative to the individual's head in the frame of reference of the image capture device. The measuring device then has means for determining the position of the light source in this frame of reference.

In an image capture step, the image capture device 10 captures at least one and preferably two images of each of the retinal reflections of said light source on the retina of the individual's two eyes, each image being captured in a corresponding image capture plane, and the relative postures of the individual's head relative to said light source being different during the two image captures.

Image capture by the image capture device is triggered by the operator, or else is triggered automatically, e.g. by an electronic and computer device.

By way of example, the electronic and computer device comprises a computer having software installed thereon for image acquisition and for processing the acquired image.

The measuring device 100 preferably possesses means for communicating with the computer that has corresponding communications means. The communications means of the measuring device 100 and of the computer may be of the wired or wireless type, and may be of any conventional design so they are not described. Advantageously, these communications means are incorporated in a common network architecture or in a point-to-point link enabling the image capture device to communicate with a plurality of computers.

The electronic and computer device may thus trigger image captures at intervals as predetermined by the operator. The measuring device 100 transmits the captured images to the electronic and computer device, which also receives the measurements of the posture parameter concerning the individual's head as performed in a step c) that is described below.

In a variant, provision may be made for the electronic and computer device to be an independent system that includes firstly a display screen for communicating the captured images and/or the results obtained during the steps of processing these images, and secondly connections enabling it to communicate these results with other appliances. Provision may also be made with an independent processing system for the system to be optionally incorporated in the measuring device 100.

By way of example, the two image captures take place in the configurations shown in FIGS. 2 and 4. These figures are diagrams showing the eyes of the individual during capture of these two images, relative to the measuring device 100.

During a first image capture, as shown in FIG. 2, a first one 21 of the LEDs 20 of the measuring device 100 is switched on and simultaneously illuminates the right eye OD and the left eye OG of the individual, as represented by light rays 23. These light rays 23 illuminate the retina in each of the individual's eyes OD and OG, so the retinas then behave as secondary light sources: the light rays are reflected in diffuse manner by the retinas and they pass back out from the eye. A portion of these light rays 23 is reflected in diffuse manner by the retinas and leaves the corresponding eye OD, OG to be received by the pupil 11 of the image capture device 10.

Similarly, during a second image capture, shown in FIG. 4, a second LED 22 of the measuring device 100 is switched on and illuminates the right and left eyes OD and OG of the individual simultaneously, as represented by light rays 24. These light rays 24 illuminate the retinas of each of the individual's eyes OD and OG. A portion of these light rays 24 is reflected by the retinas and leaves the corresponding eyes OD, OG to be received by the pupil 11 of the image capture device 10.

The corresponding images 11 and 12, as captured by the image capture device 10 thus comprise reflection images IROD1, IROG1, IROD2, IROG2 of the corresponding first and second LEDs 21 and 22 on the retina of each of the individual's eyes OD and OG.

In general, only a portion of each retinal reflection image IROD1, IROG1, IROD2, IROG2 is visible through the pupil 11 of each eye OD, OG. The portion of the image that is visible is the portion that lies in the frustoconical space extending between the individual's pupil and the pupil of the image capture device.

Figure 5:
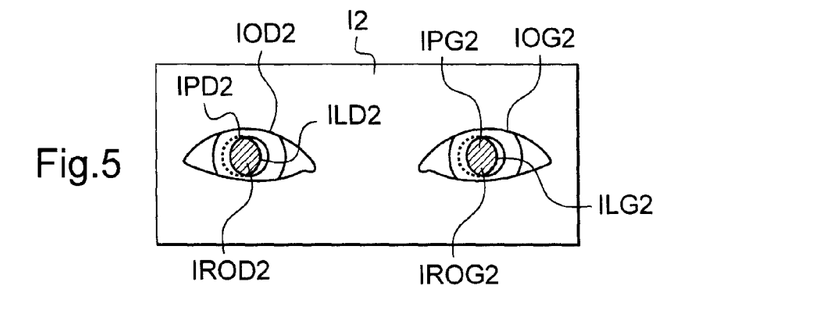
FIG. 5 is a diagrammatic view in the image capture plane of the second image as captured with reference to FIG. 4.

In this example, the image IROD1, IROG1, IROD2, IROG2 of the retinal reflection is shown shaded in the image IOD1, IOG1, IOD2, IOG2, of the corresponding eye (FIGS. 3 and 5). The outline of this image of the reflection that is not visible in the captured image is drawn as a dotted line.

The electronic and computer device acts in practice to capture a series of images, and only those images having the image of the retinal reflection visible thereon are subsequently retained. In particular, the electronic and computer device selects two images corresponding to the image entering and leaving said frustoconical space, this pair of images giving access to a maximum amount of information.

In this example, the posture of the individual's head in the frame of reference of the image capture device remains the same while images are being captured, however the postures of the individual's head relative to said light source differ between two image captures since a different LED is switched on during each image capture. For this purpose, it is possible for example to capture the two images separated by a very short time interval so that any movement of the individual within that time interval is negligible. By way of example, this time interval may lie in the range 2 milliseconds (ms) to 100 ms.

Comparing the images 11 and 12 shown diagrammatically in FIGS. 3 and 5 shows that the position of the image IROD1, IROG1 of the reflection of the LED 21 in the image 11 is different from the position of the image IROD2, IROG2 of the reflection of the LED 22 in the image 12. In other words, when the position of the light source that is switched on during image capture varies, then the position of the image of the reflection of said source also varies.

In this example, the position of the image IROD1, IROG1, IROD2, IROG2 of the reflection of each LED imaged through the pupil of the corresponding eye is represented by the boundary or limit ILD1, ILG1, ILD2, ILG2 between the illuminated zone of the image IPD1, IPG1, IPD2, IPG2 of the individual's pupil, i.e. the retinal reflection of the light source that is switched on as represented by shading in FIGS. 3 and 5, and the dark zone of the pupil that is not illuminated by the LED 21, 22. This limit ILD1, ILG1, ILD2, ILG2 corresponds to the edge of the image IROD1, IROG1, IROD2, IROG2 of the reflection of the light source.

Figure 7:
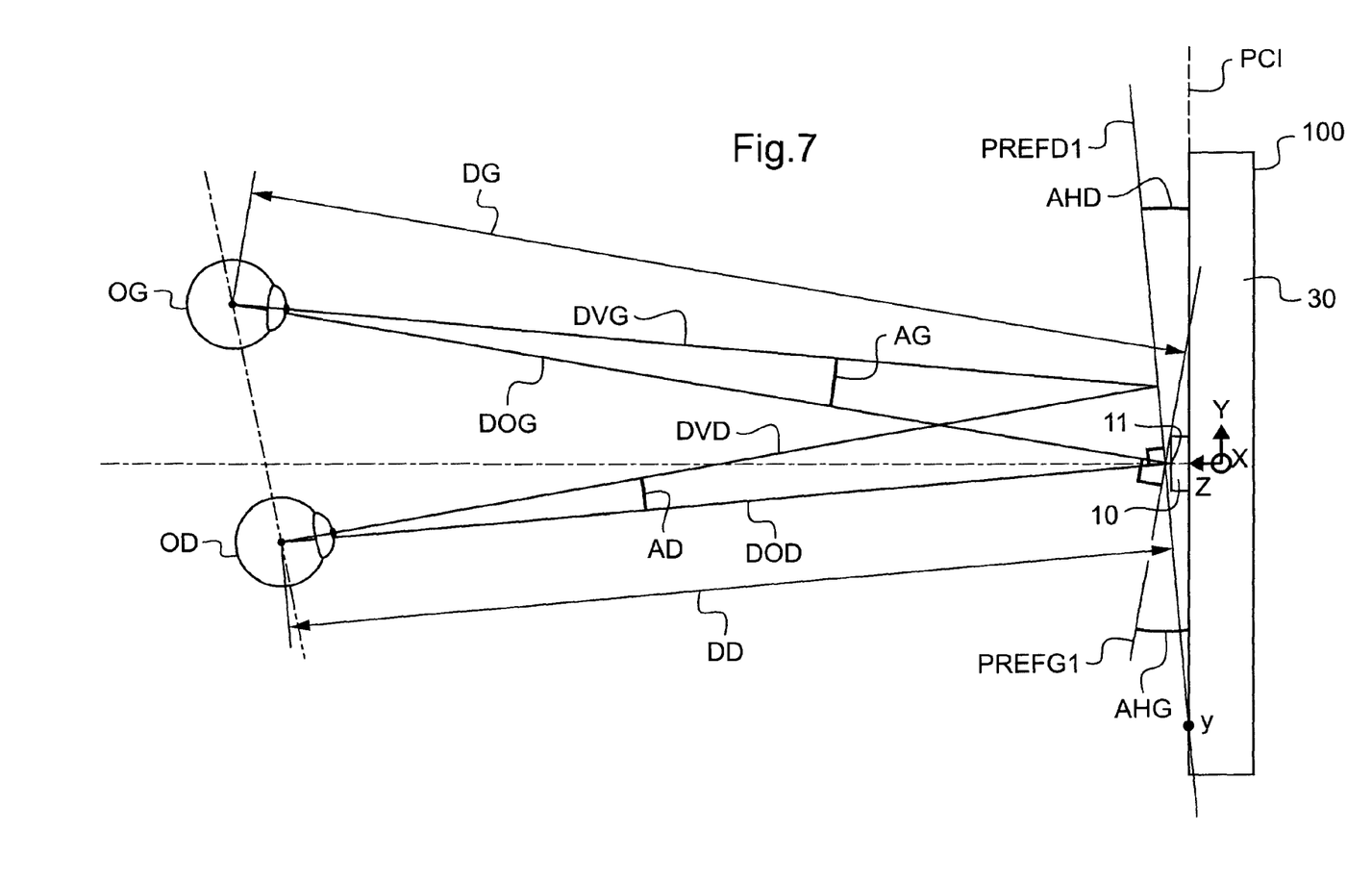
FIG. 7 is a diagrammatic plan view in a horizontal plane showing the eyes of the individual and the FIG. 1 measuring device.

The image capture step is performed when the individual is looking at the vicinity of the pupil 11 of the image capture device 10. Lines of sight DVD, DVG following the gaze direction of each of the individual's eye then preferably form an angle AD, AG that is less than or equal to a threshold value of less than 10 degrees relative to respective lines of observation DOD, DOG connecting each eye OD, OG to the pupil 11 of the image capture device 10 (FIG. 7). This condition makes it possible to ensure that the pupil of the individual's eye is imaged in satisfactory manner, so that the retinal reflections of the source on each of the individual's two eyes are visible in the two captured images.

In practice, a series of more than two images is captured by the image capture device 10. Thereafter, images are selected in which the individual is looking at the vicinity of the pupil 11 of the image capture device 10 (i.e. within a predetermined area), by calculating the gaze direction of the individual from the relative position of the corneal reflection of the light source and the pupil of the corresponding eye.

In this example, the determined area corresponds to the surface of the support situated around the pupil of the image capture device within which the angle AD, AG between the line of sight DVD, DVG in the gaze direction and the line of observation DOD, DOG is less than said threshold value.

If a plurality of images are selected, the electronic and computer device may optionally be programmed to average the images.

Alternatively, it is also possible to make provision for the method of the invention to include a verification step before the image capture step to ensure that said at least one image is captured while the image is looking at the vicinity of the pupil 11 of the image capture device 10, i.e. within a determined area. Only images for which the individual's gaze direction lies within this area are captured.

Finally, it is also possible to capture a plurality of images of the individual's head when each of the two LEDs is switched on, thus making it possible for example to average the images captured while each LED is on, and/or to capture a series of images corresponding to switching different LEDs on in succession. The accuracy of the results obtained by image processing is then improved.

In a step c) performed during said image captures, at least one parameter is measured relating to the individual's gaze direction in a frame of reference associated with the individual's head.

In this example, this gaze direction parameter consists exclusively in a parameter relating to the posture of the individual's head that is measured while the individual is gazing at the pupil of the image capture device.

In this example, it is a parameter of the posture of the head that is representative of the gaze being lowered towards the pupil of the image capture device. Since the viewing point of the eyes is close to the pupil of the image capture device, this parameter concerning the posture of the head is associated with the gaze direction, which direction may be deduced directly therefrom by calculation.

This measurement is performed for at least one of the images in each series of two or more captured images. It is described in greater detail below.

The measurement is performed either simultaneously with capturing the image, or else within a time interval that is less than or equal to 100 ms before or after image capture.

In a step e'), the electronic and computer device determine the movement of the image of the retinal reflection of the light source between the two captured images, from said signals representative of said images.

The electronic and computer device compares the movement of the image of the determined retinal reflection with the difference between the postures of the individual's head relative to the light source between the two image captures, and the refractive characteristic of the individual's eyes is deduced therefrom.

In a first variant of the method of the invention, in a step h), the results of measuring the gaze direction parameter of the individual are stored in memory in the electronic and computer device in association with the refractive characteristic deduced from the captured images under the vision conditions corresponding to said gaze direction.

The electronic and computer device then reconstitutes a map associating the gaze direction of the individual and the refractive characteristic of the eye.

In a second variant of the method of the invention, during the image capture step, the electronic and computer device does not trigger image capture unless the value of the gaze direction parameter H lies within a range corresponding to said predefined vision conditions, e.g. to near vision. The electronic and computer device then determines only the refractive characteristics of the individual's eyes when the individual is in said predefined vision condition.

This variant should clearly be envisaged only when the gaze direction parameter is obtained independently of capturing an image. This applies for example when the gaze direction parameter may be deduced directly from the posture of the individual's head, and the posture of the individual's head is determined by determination means that do not require image capture. It is also possible to envisage that a motion picture camera films the individual's head continuously and that the gaze direction parameter is calculated in parallel from the filmed images in order to trigger image capture at appropriate instants.

In a third variant of the method of the invention, the electronic and computer device selects, from among the captured images, those for which the measured gaze direction parameter presents a value that lies within a range corresponding to said predefined vision conditions, e.g. to near vision. The electronic and computer device then determines the refractive characteristics of the individual's eyes from the selected images.

In practice, and preferably, with both eyes OD and OG being illuminated simultaneously, the retinal reflection images of the light source on the retinas of each of both eyes are captured simultaneously, and in step e') the comparison is performed at least on the basis of said signals relating to the retinal reflections of both eyes as captured simultaneously in each posture of the individual's head relative to said light source.

Figure 6:
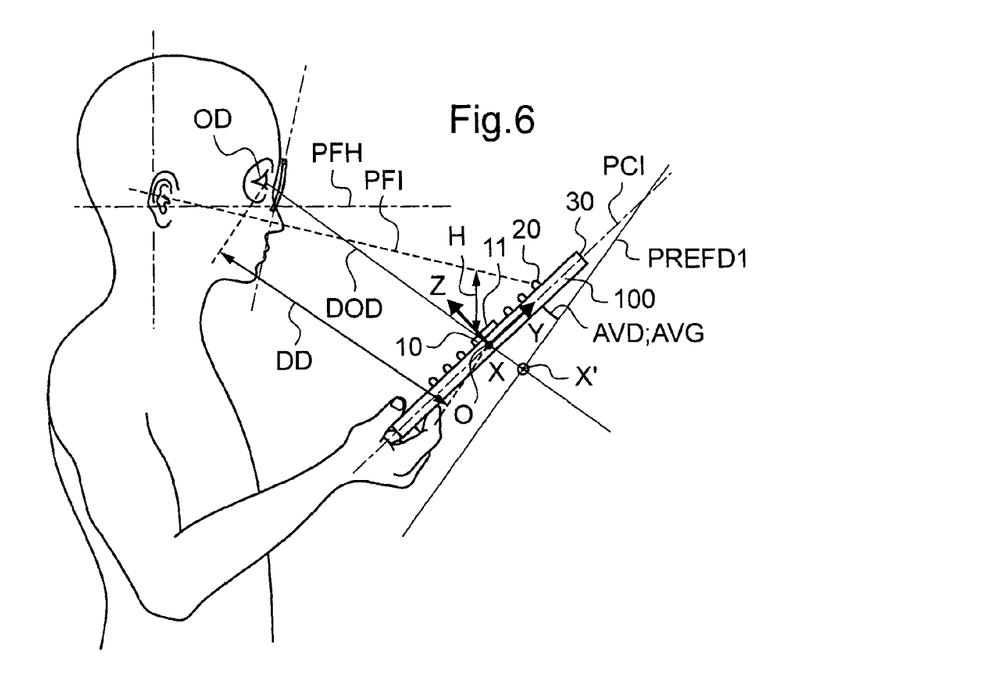
FIG. 6 is a profile view of the individual carrying the FIG. 1 measuring device in the hand.

More particularly, in step c), and as shown in FIG. 6, a measurement is made for example of a vertical distance H between the pupil 11 of the image capture device 10 and an inclined anatomical plane PFI under the vision conditions of image capture, e.g. near or intermediate vision corresponding to a horizontal anatomical plane PFH under far vision conditions.

In a variant, in step c), a distance is measured between the pupil of the image capture device and a horizon anatomical plane PFH that is substantially horizontal when the individual is in a natural posture and looking at the horizon.

In another variant, provision may be made for the gaze direction parameter to consist directly in the coordinates of the line of sight DVD, DVG as determined by the electronic and computer device on the basis of signals representative of the images of the corneal reflections of both eyes.

The following head posture parameter is also measured:
a distance DD, DG between the head or one of the individual's eyes OD, OG and the image capture device, e.g. more specifically the distance DD, DG between the centers of rotation of the individual's eyes OD, OG and the image capture device.

Provision may also be made to measure at least one of the following head posture parameters:
a first angle of inclination AVD, AVG of the image capture plane PCI relative to a first reference plane PREFD1, PREFG1 perpendicular to a line of observation DOD, DOG connecting one of the individual's eyes OD, OG and the pupil 11 of the image capture device 10 about a horizontal axis X' of said first reference plane PREFD, PREFG; and a second angle of inclination AHD, AHG of the image capture plane PCI relative to the first reference plane PREFD1, PREFG1 about an axis Y of said first reference plane PREFD1, PREFG1 perpendicular to said horizontal axis X'.

The first angle AVD, AVG thus corresponds to the angle that exists in a plane perpendicular to said horizontal axis X' between a line defined by the intersection between the image capture plane PCI and said plane perpendicular to the horizontal axis X', and a line defined by the intersection between the reference plane PREFD1, PREFG1 and said plane perpendicular to the horizontal axis X'.

The second angle AVD, AVG thus corresponds to the angle that exists in a plane perpendicular to said axis Y between a line defined by the intersection between the image capture plane PCI and said plane perpendicular to the axis Y, and a line defined by the intersection between the reference plane PREFD1, PREFG1 and said plane perpendicular to the axis Y.

In order to measure these parameters of the gaze direction H and of the posture of the individual's head, the individual's head may for example be fitted with a position-identification system such as that described in document WO 2008/132356. That position-identification system may be held directly on the wearer's head or it may be placed on an eyeglass frame that does not include ophthalmic lenses.

The ways in which the various parameters concerning posture and in particular the distance between the wearer's head and the image capture device are calculated are described in that document.

The anatomical plane PFH is advantageously Frankfurt's plane as described in that document. The inclined anatomical plane PFI corresponds to Frankfurt's plane when the individual's head is in a natural posture and the individual is looking at the image capture device and not at infinity.

In particular, a prior calibration step is performed during which the position of Frankfurt's plane is determined while the individual is looking into the distance. Frankfurt's plane is then substantially horizontal. When the individual's head is inclined, it is also possible to deduce the position of Frankfurt's plane from the geometrical characteristics of the image of a vertical position-identification element of the position-identification system as described in that document. For example, this may relate to the spacing between dark strips of a pattern shown on that vertical position-identification element.

That document also describes a method of determining the positions of the centers of rotation of an individual's eyes in the frame of reference of the individual's head. Such determination may also be performed as a calibration step.

When the individual gazes at the pupil of the image capture device, and since the positions of the centers of rotation of the eyes have been determined in the frame of reference of the head, and since the position of the head has been determined in the frame of reference of image capture, it is possible to deduce therefrom the positions of the centers of rotation of the eyes in the image capture frame of reference. If the individual looks at the pupil of the image capture device, it is possible to deduce therefrom the gaze directions of the individual's eyes and also the position of the pupil of the image capture device relative to the inclined Frankfurt's plane.

In a variant, use may also be made of a method of estimating the posture of the wearer's head in three dimensions using the method described in the document "Real-time modeling of face deformation for 3D head pose estimation" published by M. Oka et al., in the book "Analysis and modeling of faces and gestures", published by Springer in 2005, pp. 308 to 320.

It is also possible to envisage using any "eye tracking" method known to the person skilled in the art for determining the gaze direction parameter, such as the method described in document US 2003/0169907.

Typically, in an eye tracking method, an image is processed in order to determine the coordinates of the reflections of the light source on the retina of each of the individual's eyes. That step is performed for example by convolution between the image and a theoretical pattern for the reflection. The coordinates of the reflections may be determined, for example, in terms of pixel coordinates of the image representing the reflection.

The edge of the pupil is detected, e.g. by detecting outlines by means of a gradient and a Hough transform, thus making it possible to determine the coordinates of the center of the pupil and its diameter.

A calibration step also makes it possible to determine the polynomial or other relationship that converts the position of the reflection of the source and the coordinates of the center of the pupil into an angle for the gaze direction. To do this, during this calibration step, the individual gazes on sighting points of known 3D position in the image capture frame of reference, or at least of known angular position in said frame of reference.

Another calibration method consists in calculating the position of the pupil in two dimensions in a plane parallel to the frame of reference associated with the individual's head. In particular, this plane parallel to the frame of reference attached to the individual's head may be a forehead plane perpendicular to said Frankfurt's plane.

Advantageously, the electronic and computer device also stores in memory the measured head posture parameters as well as the gaze direction parameter. The refractive characteristic can thus be calculated and possibly subsequently corrected as a function of these head posture parameters.

For example, when the line of sight DVD, DVG in the gaze direction of the individual is at an angle theta with the line of observation DOD, DOG connecting the individual's eye to the pupil of the image capture device, then the image of the individual's pupil on the captured image is not circular, but rather elliptical. The computer is then programmed to divide the minor diameter of the ellipse by a factor equal to the cosine of said angle theta in order to reconstruct the real shape of the pupil, and thus of the reflection of the image of the light source. This makes it possible to determine more accurately the refractive characteristic at the end of the corresponding image processing.

In practice, in step e'), the electronic and computer device compares the movement direction of the image of the retinal reflection of the source in the two images corresponding to different positions of the light source with the movement direction of the source itself between the two corresponding image captures.

In the example shown in FIGS. 2 to 5, the source moves from the location of the LED 21 to the location of the LED 22, i.e. from left to right in the frame of reference of the wearer's head, along an axis that is substantially horizontal in the frame of reference of the individual's head.

The image IROD2, IROG2 of the retinal reflection of the LED 22 imaged through the pupil of each of the individual's eyes is offset a little to the left in this frame of reference relative to the image IROD1, IROG1 of the retinal reflection of the LED 21.

The image of the IROD1, IROG1 of the retinal reflection is thus moved in a direction opposite to the direction of the movement of the light source, along an axis of the eye that is parallel to the movement axis of the on LED. In this example, these axes are substantially horizontal.

In accordance with the principle of skiascopy, the electronic and computer device is programmed to deduce from this comparison that the eyes OD and OG of the individual present negative ametropia, i.e. myopia, along a meridian of the eye perpendicular to the axis of the eye parallel to the movement axis of the on LED, i.e. in this example along the vertical meridian.

When the movement of the image of the reflection takes place in the same direction as the movement of the light source, the electronic and computer device is programmed to deduce from this comparison that the eyes OD and OG of the individual present positive ametropia, i.e. hypermetropia along the corresponding meridian.

In this example, the arrangement of the LEDs 20 in the plane of the measuring device makes it possible to determine the sign of the ametropia of each eye along four meridians of the eye, including two meridians oriented at 45 degrees from a first meridian and one meridian oriented at 90 degrees from that first meridian, by successively switching on at least two LEDs arranged on each of the four directions in which LEDs are aligned on the front face of the support 30.

In a variant, in a step e), the electronic and computer device uses the signal representative of at least one image and preferably the signals representative of each of the images to determine the width of the image IROD1, IROG1, IROD2, IROG2 of the retinal reflection of the light source, and deduces therefrom a value for the ametropia of the individual's eyes.

In this example, since the light sources are LEDs, the image is circular in shape.

For an eye that does not present astigmatism, the image of the retinal reflection of the source is thus circular in shape. The width of the image of the retinal reflection then corresponds to the diameter of the reflection.

When the eye does indeed present astigmatism, the image of the retinal reflection presents an elliptical shape. The axis of the ellipse that has the greatest diameter then corresponds to the meridian of the eye that presents the greatest ametropia in absolute value. The width of the image of the retinal reflection then corresponds to the greatest diameter of said ellipse.

In order to determine this width, the electronic and computer device analyzes each captured image to determine the spatial distribution of the intensity of the retinal reflection of the corresponding source. This spatial distribution of intensity is shown diagrammatically in FIG. 8. Each curve in FIG. 8 corresponds to a proportion of light reflected by the eye.

Figure 8:
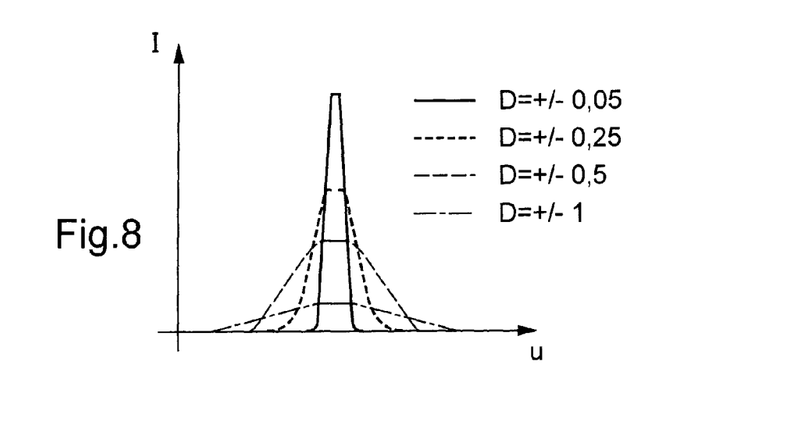
FIG. 8 is a diagram showing the spatial distribution of intensity of the retinal reflection of the corresponding source.

The points situated on the plateau of each curve corresponds to a reflection covering the entire surface area of the pupil, whereas the points situated on the slopes of each curve correspond to a reflection having an edge that is visible in the pupil of the eye, as shown in FIGS. 3 and 5. The spatial distribution of intensity is shown in this figure for different values of ametropia D expressed in terms of diopters in the legend.

In this example, the spatial intensity distribution is equal to a percentage of the area of the pupil illuminated by the reflection of the light source.

In order to determine this percentage, the electronic and computer device determines the shape of the pupil of the eye and the position of the boundary or limit between the zone of the image of the pupil of the eye that is illuminated by the reflection of the light source, and the dark zone of the pupil of the individual's eye. This percentage is determined with increasing accuracy when the shape of the pupil of the eye is known precisely, as mentioned above.

The electronic and computer device then determines the diameter of the retinal reflection corresponding to each intensity distribution, e.g. as being equal to the width at half height of the spatial distribution of intensity (i.e. the full width at half maximum).

If the shape of the retinal reflection is elliptical, then the electronic and computer device determines the spatial distribution of intensity along the major axis of the ellipse and deduces the width of the retinal reflection therefrom.

In practice, the real quality of the eye and the dimensions of the source may cause the spatial distribution of intensity as observed on the captured images to vary, and in particular may spread said distribution. The electronic and computer device may advantageously be programmed to correct for such variations, in particular by means of a calibration step. The calibration step may for example be performed with the help of an artificial eye presenting known aberration, in a manner well known to the person skilled in the art.

Advantageously, the electronic and computer device reconstitutes the spatial distribution of the intensity of the reflection from a plurality of captured images, each showing a portion of the distribution. Provision may be made in particular for the series of captured images to enable the movement of the image of the retinal reflection of the source to be tracked so as to be visualized in full, and to obtain the complete spatial distribution of intensity of the retinal reflection of the source.

The electronic and computer device thus determines very accurately the width of the image of the retinal reflection.

The width L of the image of the retinal reflection of the source satisfies the following relationship:

$$L=E*(-2*D*DPR+DPR/DSP-1)$$

where:

E is the diameter of the pupil of the individual's eye under consideration;

DPR is the distance between the pupil of the image capture device and the retina of the individual's eye;

DSR is the distance between the light source and the retina of the individual's eye; and D is the value of the eye's ametropia in diopters.

The value D of the ametropia may thus be calculated by using the following formula:

$$D=(L/E-DPR/DPS+1)/(-2DPR)$$

The diameter of the pupil of the individual's eye may either be input by the user as a calculation parameter into the electronic and computer device, or else it may be measured from the captured images, e.g. by performing the above-described image processing of the eye tracking method.

In the first option, the user inputs a predetermined mean value for the size of the pupil. In the second option, the electronic system for processing the image identifies the pupil of at least one eye of the individual in at least one image in a series of recorded images, and it measures its diameter. From that it deduces the real size of the pupil by multiplying the diameter as measured in this way by a scale factor. The scale factor is determined for example by using the position-identifying system and the method as described in document WO 2008/132356.

The distance DPR between the pupil of the image capture device and the retina of an eye of the individual is determined from the posture parameters measured in step c). These posture parameters include in particular the distance DD, DG between the center of rotation of each of the individual's eyes OD, OG and the image capture device.

Since the distance between the retina and the center of rotation of an eye is equal to about 11 mm, the distance DPR between the pupil of the image capture device and the retina of an eye of the individual is equal to the distance DD, DG between the center of rotation of an eye OD, OG of the individual and the image capture device plus a distance of 11 mm.

The distance DSR between the light source and the retina of the individual's eye is calculated by the electronic and computer device from the distance DPR between the pupil of the image capture device and the retina of an eye of the individual, and the position of the light source that was switched on while the image was being captured relative to the pupil of the image capture device, which distance is known.

In the presently-described example, the distances DPR and DSR are very similar, and in a first approximation they may be considered to be equal.

The value of the ametropia, i.e. the spherical or cylindrical power of the eye, is thus calculated using the above formula.

In order to accelerate implementation of the method of the invention, it is advantageous to perform image captures of the individual's eyes that gives as much information as possible about the size and the shape of the retinal reflection of the source that is on, i.e. that makes it possible to visualize as clearly as possible the edges of the retinal reflection.

By way of example, the capture of a first series of images is performed by switching on in succession the LED's that are situated on a single alignment direction, in a sequence of alternating LEDs situated on either side of the pupil 11 of the image capture device 10, beginning with the LEDs located closest to the pupil 11 and moving progressively away therefrom. The step-size between two LEDs that are switched on in succession on the same side may, for example, be doubled at each iteration, so as to scan rapidly through all of the LEDs corresponding to the alignment direction under consideration.

Thereafter, the following image captures are performed by switching on only those LEDs for which the intensity of the reflection is equal on average to 50% and 90% of the maximum intensity of the reflection. When the intensity of the reflection is equal to 50% of the maximum intensity of the reflection, the edge of the reflection, i.e. the boundary or limit between the zone of the pupil of the eye that is illuminated by the reflection and the zone of the pupil of the eye that is not illuminated divides the pupil of the eye into two zones of equal areas. This corresponds to switching on four LEDs that are in alignment on either side of the pupil of the image capture device.

The width of the reflection can thus be determined more accurately.

In order to determine the astigmatism of the eye, the electronic and computer device analyzes the shape of the reflection and determines the spatial distributions of the intensity of the reflection, and thus the value of ametropia along different meridians of the eye, e.g. along three meridians selected arbitrarily and arranged relative to one another at angles of 0, 45, and 90 degrees.

Thereafter, the electronic and computer device performs other measurements along the meridians of the eye corresponding to the smallest and the largest values for ametropia, i.e. it determines the smallest and the largest diameters of the ellipse. From that it deduces accurate values for ametropia along the two corresponding diameters, since the diameter of the ellipse varies little around the major and minor axes of the ellipse.

Finally, it determines the diameters of the ellipse at 45 degrees on either side of the major axis of the ellipse. This measurement serves to determine accurately the axis of the astigmatism since the value of the diameter of the ellipse varies rapidly around the axis situated at 45 degrees to the major axis. Astigmatism is thus determined very accurately.

In the above, the individual is not wearing an eyeglass frame that contains correcting ophthalmic lenses. The value of the refractive characteristic that is obtained is thus a value that corresponds to the individual's own eyes. In a variant, it is possible to envisage the operator placing vision correction equipment on said individual's face, e.g. including ophthalmic lenses of known power and deflection.

Under such circumstances, the electronic and computer device is programmed to correct the signals representative of the captured images and/or the refractive characteristic deduced from said signals as a function of the power and the deflection of the vision correction equipment.

For example, in the simple situation of a spherical vision correction lens of given power, that amounts to adding that power to the value of the ametropia as determined by the above-described method. The sum of those two values gives the refractive characteristic of the eyes of the individual.

It is then also possible to apply the method of the invention once more in order to determine any over-correction or under-correction of the individual's eyes.

Naturally, the individual may also be wearing eyeglass frames that do not include vision correction lenses. Such a frame serves for example as a support for the position-identifying system used in order to determine the posture parameter(s) of the individual's head.

The gaze direction of the individual in the frame of reference of the image capture device preferably remains the same while the images are being captured. For this purpose, the electronic and computer device triggers image captures at intervals that are very short, e.g. at intervals of 100 ms, such that the individual's eyes move little between two image captures.

The present invention is not limited in any way to the embodiments described and shown, and the person skilled in the art knows how to apply any variation thereto in accordance with its spirit.

In particular, the measuring device may in a variant include an ultrasound measuring device that comprises at least one emitter and at least one receiver of ultrasound, or it may include a measuring device having electromagnetic sensors, for measuring posture parameters relating to the individual's head.

In a variant, in step e), said at least one captured image is used to determine a distribution of the luminance of the image IROD1, IROG1, IROD2, IROG2 of the retinal reflection of the light source 20, and said refractive characteristic D of the individual's eyes OD, OG is determined as a function of this distribution of luminance.

The refractive characteristic is then determined by a conventional photorefraction method such as that described in the article published in "Optometry and Vision Science", Vol. 174, pp. 472 to 482, in 1997. The refractive characteristic of the eye, here its sign and/or the value of its ametropia, is determined from the distribution of the luminance of the image of the reflection. This is achieved by using a prior calibration step.

The various implementations and their variants described with reference to the method of calculating the refractive characteristic by skiascopy apply in similar manner to the method using a method of calculating the refractive characteristic of photorefraction.

For example, it is possible to envisage implementing the method of the invention by capturing at least two images of the retinal reflection of said light source on the retinas of both of the individual's eyes, during said image capture step, and determining said refractive characteristic of one of the two eyes of the individual from one of the images and determining the refractive characteristic of the individual's other eye from the other image.

In another variant, the method of the invention includes a psychophysical test performed by implementing the following steps:

r) displaying in front of the individual's eyes an image that presents fuzziness corresponding to low pass filtering by a frequency filter of given cutoff for filtering the spatial frequencies of the image;

t) storing in memory the refractive characteristic as determined in association with the result of the psychophysical test performed in step s) and the value of the cutoff frequency of the lowpass filter used in step r); and u) reiterating at least steps b) and c) together with the image capture step for determining a refractive characteristic and steps r) and t) for different cutoff frequencies of the image filter.

The psychophysical test preferably also includes a step s) of characterizing the perception of the fuzziness of the image by the individual, and in step u), the result of this test is also stored in memory in association with the cutoff frequency of the corresponding filter.

For this purpose, the measuring device 100 includes means for generating an image presenting fuzziness in the display and a device for displaying the image. By way of example, the display means are constituted by a screen incorporated in the housing of the above-described device and adapted to display said fuzzy image.

By way of example, the fuzzy image is generated by the electronic and computer device. It is obtained by spatially filtering a portion of the spatial frequencies of a sharp image, e.g. an image representing an alphanumeric character. The electronic and computer device determines the fuzzy image by digitally applying a lowpass filter having a predetermined cutoff frequency to the sharp image.

It is also possible to envisage that the fuzzy image is obtained by analog filtering of screen display signals.

In general, the fuzzy image may be obtained, in a variant, by any method known to the person skilled in the art, in particular by any image processing that enables a fuzzy image to be obtained.

The sharp image may be subdivided into a plurality of different spatial frequency components.

During filtering, the amplitudes of the components that present high spatial frequencies are attenuated. The outlines of the alphanumeric character displayed on the image thus appear diffuse.

The lowpass filter used is characterized by a cutoff spatial frequency that corresponds to a threshold above which the spatial frequencies of the image are more strongly attenuated than are the spatial frequencies of the image below said threshold. The cutoff spatial frequency thus corresponds to the minimum distance between two details of the fuzzy image that can be distinguished.

The fuzzy image may be calculated in real time or it may be recorded in a library of images in the electronic and computer device.

The electronic and computer device communicates with the screen in order to cause it to display the calculated fuzzy image.

Step s) of characterizing the perception of the fuzzy image may, for example, consist in asking the individual questions about his or her perception of the fuzziness of the displayed image. By way of example, the questions asked may seek to determine whether or not the individual detects fuzziness in the image, to evaluate any difficulty felt by the individual as a result of the fuzziness, and/or any loss of readability in the alphanumeric character as represented by the fuzzy image.

The individual's answers to the questions asked characterize the individual's perception of the fuzziness in terms of the degree of fuzziness of the displayed image. The answers are stored in the memory of the electronic and computer device in association with the determined refractive characteristic and with the value of the cutoff frequency of the lowpass filter used in step r).

In addition, in the method in accordance with the invention, at least steps b) and c) together with the image capture steps for determining a refractive characteristic and steps r) to t) at different cutoff frequencies for the image filter are reiterated.

Advantageously, it is then possible to determine how the perception of fuzziness varies and how the refractive characteristic of the individual's eyes vary as the degree of image fuzziness varies.

An implementation of the invention is described above in detail in which the refractive characteristics of both eyes are determined from at least one image, e.g. from a single series of images.

In a variant, it is possible to envisage that:

during said image capture step, at least two images are captured, each comprising images of two retinal reflections of said light source on the retinas of both eyes of the individual; and on the basis of one of these two images, said refractive characteristic of one of the two eyes of the individual is determined, and on the basis of the other image, the refractive characteristic of the other of the individual's eyes is determined.

For example, it is possible to envisage that a series of images is captured and that some of those images are processed in order to determine the refractive characteristic of one eye and others of those images are processed in order to determine the refractive characteristic of the other eye. The remainder of the method of the invention remains unchanged.

Under such circumstances, it is possible to refine the choice of processed images for each eye independently, this making it possible for example to select for each eye specifically those captured images for which the intensity of the reflection is equal on average to 50% and to 90% of the maximum intensity of the reflection.

This is useful in particular when the two eyes present very different degrees of ametropia.

The invention claimed is:

1. A method of automatically measuring at least one refractive characteristic of both eyes (OD, OG) of an individual, the method comprising the following steps:

a) adjusting at least one posture of the individual's head in accordance with the wishes of said individual, in a frame of reference (O, X, Y, Z) associated with an image capture device (10) that is adapted to convert each captured image into a signal that is representative thereof;

b) illuminating both eyes (OD, OG) by means of at least one light source (20) of known position in said frame of reference (O, X, Y, Z) associated with the image capture device (10);

c) measuring at least one gaze direction parameter (H) associated with the gaze direction of the individual in a frame of reference associated with the individual's head;

d) using said image capture device (10) to capture at least one image (IROD1, IROG1, IROD2, IROG2) of the retinal reflection of said light source (20) on the retinas of both eyes (OD, OG) of the individual, corresponding to the gaze direction parameter measured in step c);

f) from said at least one image captured in step d), determining said refractive characteristic (D) for each of the eyes (OD, OG) of the individual; and h) storing the gaze direction parameter (H) associated with the gaze direction of the individual as measured during the image capture of step d) in association with the determined refractive characteristic;

wherein, in step c), at least one of the following posture parameters (DD, DG, H, AHD, AHG, AVD, AVG) of the head are measured:

a vertical distance (H) between a pupil of the image capture device (10) and an anatomical plane (PFI) of the individual that is inclined when the individual is in a natural posture and is looking towards the image capture device, said plane corresponding to a horizon anatomical plane (PFH) that is substantially horizontal when the individual is in a natural posture and looking at the horizon;

a distance between a pupil of the image capture device (10) and the horizon anatomical plane (PFH) that is substantially horizontal when the individual is in a natural posture and looking at the horizon;

a first angle of inclination (AVD, AVG) of the image capture plane (PCI) relative to a first reference plane (PREFD1, PREFG1) perpendicular to the line connecting one of the individual's eyes (OD, OG) with the pupil of the image capture device (10) in a plane perpendicular to a horizontal axis (X') of said first reference plane, which angle corresponds to the angle that exists between a line defined by the intersection between the image capture plane (PCI) and said plane perpendicular to the horizontal axis (X'), and a line defined by the intersection between the reference plane (PREFD1, PREFG1) and said plane perpendicular to the horizontal axis (X'); and a second angle of inclination (AHD, AHG) of the image capture plane (PCI) relative to said first reference plane (PREFD1, PREFG1) in a plane perpendicular to an axis (Y) of said first reference plane (PREFD1, PREFG1) perpendicular to said horizontal axis (X'), which corresponds to the angle that exists in said plane perpendicular to said axis (Y) between a line defined by the intersection between the image capture plane (PCI) and said plane perpendicular to the axis (Y), and a line defined by the intersection between the reference plane (PREFD1, PREFG1) and said plane perpendicular to the axis (Y).

2. A method according to claim 1, further including the following steps:

e) determining from said at least one captured image a width or a luminance distribution of the image (IROD1, IROG1, IROD2, IROG2) of the retinal reflection of the light source (20), and determining said refractive characteristic (D) of each of the individual's eyes (OD, OG) as a function of said width or said luminance distribution.

3. A method according to claim 2, wherein both eyes (OD, OG) are illuminated simultaneously, and the images of the retinal reflections of the light source (20) on the retinas of both eyes (OD, OG) are captured simultaneously, and in step e), the width or the luminance distribution of the image (IROD1, IROG1, IROD2, IROG2) of the retinal reflection of the light source (20) is determined at least from said signals relating to the retinal reflections of both eyes (OD, OG) as captured simultaneously in said posture of the individual's head relative to said light source (20).

4. A method according to claim 3, wherein a value is deduced for the ametropia of each of the individual's eyes (OD, OG) from the width (L) or from the luminance distribution of the image (IROD1, IROG1, IROD2, IROG2) of the retinal reflection of the light source (20).

5. A method according to claim 1, wherein at least two images (IROD1, IROG1, IROD2, IROG2) are captured of the retinal reflections of said light source (20) on the retina of each of the individual's two eyes (OD, OG), and the method further includes the following step:

e') determining from said at least two captured images a movement of the image (IROD1, IROG1, IROD2, IROG2) of the retinal reflection of the light source (20);

said refractive characteristic (D) of each of the individual's eyes (OD, OG) being determined as a function of said movement.

6. A method according to claim 5, wherein:

for the posture of the individual's head relative to said light source (20) differing during the two image captures;

in step c), during said image captures, at least one posture parameter (DD, DG, AHD, AHG, AVD, AVG) of the individual's head is measured in the frame of reference (O, X, Y, Z) of the image capture device (10); and in step e'), the movement of the image of the determined retinal reflection is compared with the difference in posture of the individual's head relative to the light source (20) between the two image captures as a function of said head posture parameter (DD, DG, AHD, AHG, AVD, AVG) measured in step c);

said refractive characteristic (D) of each of the individual's eyes (OD, OG) being deduced from the comparison.

7. A method according to claim 6, wherein the sign of the ametropia of each of the individual's eyes (OD, OG) is deduced from said comparison.

8. A method according to claim 6, wherein both eyes (OD, OG) are illuminated simultaneously, and the images of the retinal reflections of the light source (20) on the retinas of both eyes (OD, OG) are captured simultaneously, and wherein, in step e'), the movements of the images (IROD1, IROG1, IROD2, IROG2) of the retinal reflections of the light source (20) are determined at least from said signals relating to the retinal reflections of both eyes (OD, OG) as captured simultaneously in each posture of the individual's head relative to said light source (20).

9. A method according to claim 1, wherein, during image capture, a support (30) on which said light source (20) and said image capture device (10) are mounted is carried by said individual in the hand.

10. A method according to claim 1, including a verification step before or after the image capture step for verifying that said at least one image is captured while the individual is looking in the vicinity of a pupil (11) of the image capture device (10), i.e. looking within a determined area in the vicinity of the pupil.

11. A method according to claim 1, wherein said gaze direction parameter consists exclusively in a posture parameter (H) of the individual's head as measured while the individual is gazing at the pupil of the image capture device.

12. A method according to claim 2, wherein, during a preliminary step before capturing at least one image, vision correction equipment is placed on the face of said individual and wherein the signals representing said captured image and/or the refractive characteristic deduced from said signals is corrected as a function of the power and the deflection of the vision correction equipment.

13. A method according to claim 5, wherein, during a preliminary step before capturing at least one image, vision correction equipment is placed on the face of said individual and wherein the signals representing said captured image and/or the refractive characteristic deduced from said signals is corrected as a function of the power and the deflection of the vision correction equipment.

14. A method according to claim 1, wherein, in step c), the individual's gaze direction (DVD, DVG) is calculated from the signals representative of the images of the corneal reflections of both eyes (OD, OG).

15. A method according to claim 1, comprising the following steps:
   r) before or during the capture of at least one image, displaying a reference image before the individual's eyes, the reference image presenting fuzziness corresponding to lowpass filtering by a frequency filter of given cutoff for filtering the spatial frequencies of said reference image;
   t) storing in memory the refractive characteristic as determined in association with the value of the cutoff frequency of the lowpass filter used in step r) for filtering the reference image; and
   u) reiterating at least steps b), c), d), f), r), and t) for different cutoff frequencies of the reference image filter.

16. A method according to claim 1, wherein:
   during said image capture step, at least two images are captured in succession, each corresponding to the images of the two retinal reflections of said light source on the retinas of both eyes of the individual; and
   from one of said two images, determining said refractive characteristic of one of the two eyes of the individual, and from the other image, determining the refractive characteristic of the other eye of the individual.

17. A method of automatically measuring at least one refractive characteristic of both eyes (OD, OG) of an individual under predefined vision conditions, the method comprising the following steps:
   a) adjusting at least one posture of the individual's head in accordance with the wishes of said individual, in a frame of reference (O, X, Y, Z) associated with an image capture device (10) adapted to convert each captured image into a signal that is representative thereof;
   b) illuminating both eyes (OD, OG) by means of at least one light source (20) of known position in said frame of reference (O, X, Y, Z) associated with the image capture device (10);
   c) measuring at least one gaze direction parameter (H) associated with the gaze direction of the individual in a frame of reference associated with the individual's head;
   i) comparing the gaze direction parameter measured in step c) with a range of values corresponding to the predefined vision conditions and, if the value of said gaze direction parameter (H) as measured in step c) is situated in said range corresponding to said predefined vision conditions, triggering the capture by said image capture device (10) of at least one image (IROD1, IROG1, IROD2, IROG2) of the retinal reflection of said light source (20) on the retinas of both eyes (OD, OG) of the individual, the image being captured in an image capture plane (PCI); and
   j) determining from said at least one captured image, said refractive characteristic (D) of each of the eyes (OD, OG) of the individual in said predefined vision conditions;
   wherein, in step c), at least one of the following posture parameters (DD, DG, H, AHD, AHG, AVD, AVG) of the head are measured:
      a vertical distance (H) between a pupil of the image capture device (10) and an anatomical plane (PFI) of the individual that is inclined when the individual is in a natural posture and is looking towards the image capture device, said plane corresponding to a horizon anatomical plane (PFH) that is substantially horizontal when the individual is in a natural posture and looking at the horizon;
      a distance between a pupil of the image capture device (10) and the horizon anatomical plane (PFH) that is substantially horizontal when the individual is in a natural posture and looking at the horizon;
      a first angle of inclination (AVD, AVG) of the image capture plane (PCI) relative to a first reference plane (PREFD1, PREFG1) perpendicular to the line connecting one of the individual's eyes (OD, OG) with the pupil of the image capture device (10) in a plane perpendicular to a horizontal axis (X') of said first reference plane, which angle corresponds to the angle that exists between a line defined by the intersection between the image capture plane (PCI) and said plane perpendicular to the horizontal axis (X'), and a line defined by the intersection between the reference plane (PREFD1, PREFG1) and said plane perpendicular to the horizontal axis (X'); and
      a second angle of inclination (AHD, AHG) of the image capture plane (PCI) relative to said first reference plane (PREFD1, PREFG1) in a plane perpendicular to an axis (Y) of said first reference plane (PREFD1, PREFG1) perpendicular to said horizontal axis (X'), which corresponds to the angle that exists in said plane perpendicular to said axis (Y) between a line defined by the intersection between the image capture plane (PCI) and said plane perpendicular to the axis (Y), and a line defined by the intersection between the reference plane (PREFD1, PREFG1) and said plane perpendicular to the axis (Y).

18. A method according to claim 17, further including the following steps:
   e) determining from said at least one captured image a width or a luminance distribution of the image (IROD1, IROG1, IROD2, IROG2) of the retinal reflection of the light source (20), and determining said refractive characteristic (D) of each of the individual's eyes (OD, OG) as a function of said width or said luminance distribution.

19. A method according to claim 18, wherein both eyes (OD, OG) are illuminated simultaneously, and the images of the retinal reflections of the light source (20) on the retinas of both eyes (OD, OG) are captured simultaneously, and in step e), the width or the luminance distribution of the image (IROD1, IROG1, IROD2, IROG2) of the retinal reflection of the light source (20) is determined at least from said signals relating to the retinal reflections of both eyes (OD, OG) as captured simultaneously in said posture of the individual's head relative to said light source (20).

20. A method according to claim 19, wherein a value is deduced for the ametropia of each of the individual's eyes (OD, OG) from the width (L) or from the luminance distribution of the image (IROD1, IROG1, IROD2, IROG2) of the retinal reflection of the light source (20).

21. A method according to claim 17, wherein at least two images (IROD1, IROG1, IROD2, IROG2) are captured of the retinal reflections of said light source (20) on the retina of each of the individual's two eyes (OD, OG), and the method further includes the following step:

e') determining from said at least two captured images a movement of the image (IROD1, IROG1, IROD2, IROG2) of the retinal reflection of the light source (20);
said refractive characteristic (D) of each of the individual's eyes (OD, OG) being determined as a function of said movement.

22. A method according to claim 21, wherein:

for the posture of the individual's head relative to said light source (20) differing during the two image captures;
in step c), during said image captures, at least one posture parameter (DD, DG, AHD, AHG, AVD, AVG) of the individual's head is measured in the frame of reference (0, X, Y, Z) of the image capture device (10); and
in step e'), the movement of the image of the determined retinal reflection is compared with the difference in posture of the individual's head relative to the light source (20) between the two image captures as a function of said head posture parameter (DD, DG, AHD, AHG, AVD, AVG) measured in step c);
said refractive characteristic (D) of each of the individual's eyes (OD, OG) being deduced from the comparison.

23. A method according to claim 22, wherein the sign of the ametropia of each of the individual's eyes (OD, OG) is deduced from said comparison.

24. A method according to claim 21, wherein both eyes (OD, OG) are illuminated simultaneously, and the images of the retinal reflections of the light source (20) on the retinas of both eyes (OD, OG) are captured simultaneously, and wherein, in step e'), the movements of the images (IROD1, IROG1, IROD2, IROG2) of the retinal reflections of the light source (20) are determined at least from said signals relating to the retinal reflections of both eyes (OD, OG) as captured simultaneously in each posture of the individual's head relative to said light source (20).

25. A method according to claim 17, wherein, during image capture, a support (30) on which said light source (20) and said image capture device (10) are mounted is carried by said individual in the hand.

26. A method according to claim 17, including a verification step before or after the image capture step for verifying that said at least one image is captured while the individual is looking in the vicinity of a pupil (11) of the image capture device (10), i.e. looking within a determined area in the vicinity of the pupil.

27. A method according to claim 17, wherein said gaze direction parameter consists exclusively in a posture parameter (H) of the individual's head as measured while the individual is gazing at the pupil of the image capture device.

28. A method according to claim 18, wherein, during a preliminary step before capturing at least one image, vision correction equipment is placed on the face of said individual and wherein the signals representing said captured image and/or the refractive characteristic deduced from said signals is corrected as a function of the power and the deflection of the vision correction equipment.

29. A method according to claim 21, wherein, during a preliminary step before capturing at least one image, vision correction equipment is placed on the face of said individual and wherein the signals representing said captured image and/or the refractive characteristic deduced from said signals is corrected as a function of the power and the deflection of the vision correction equipment.

30. A method according to claim 17, wherein, in step c), the individual's gaze direction (DVD, DVG) is calculated from the signals representative of the images of the corneal reflections of both eyes (OD, OG).

31. A method according to claim 17, comprising the following steps:

r) before or during the capture of at least one image, displaying a reference image before the individual's eyes, the reference image presenting fuzziness corresponding to lowpass filtering by a frequency filter of given cutoff for filtering the spatial frequencies of said reference image;
t) storing in memory the refractive characteristic as determined in association with the value of the cutoff frequency of the lowpass filter used in step r) for filtering the reference image; and
u) reiterating at least steps b), c), i), j), r), and t) for different cutoff frequencies of the reference image filter.

32. A method according to claim 17, wherein:

during said image capture step, at least two images are captured in succession, each corresponding to the images of the two retinal reflections of said light source on the retinas of both eyes of the individual; and
from one of said two images, determining said refractive characteristic of one of the two eyes of the individual, and from the other image, determining the refractive characteristic of the other eye of the individual.

33. A device for automatically measuring at least one refractive characteristic of both eyes (OD, OG) of an individual, the device comprising:

a support (30);
at least one light source (20) mounted on the support (30) in such a manner as to illuminate at least one of the individual's eyes (OD, OG);
at least one image capture device (10) mounted on said support (30), adapted to capture at least one image (IROD1, IROG1, IROD2, IROG2) of the retinal reflection of said light source (20) on the retina of each eye of the individual and to convert each captured image into a signal that is representative thereof, said light source (20) being of known position in a frame of reference (O, X, Y, Z) associated with said image capture device (10);
means for measuring at least one gaze direction parameter (H) associated with the individual's gaze direction in a frame of reference associated with the individual's head, the parameter being selected from the following parameters:
a vertical distance (H) between a pupil of the image capture device (10) and an anatomical plane (PFI) of the individual that is inclined when the individual is in a natural posture and is looking towards the image capture device, said plane corresponding to a horizon anatomical plane (PFH) that is substantially horizontal when the individual is in a natural posture and looking at the horizon;
a distance between a pupil of the image capture device (10) and the horizon anatomical plane (PFH) that is substantially horizontal when the individual is in a natural posture and looking at the horizon;
a first angle of inclination (AVD, AVG) of the image capture plane (PCI) relative to a first reference plane (PREFD1, PREFG1) perpendicular to the line connecting one of the individual's eyes (OD, OG) with the pupil of the image capture device (10) in a plane perpendicular to a horizontal axis (X') of said first reference plane, which angle corresponds to the angle that exists between a line defined by the intersection between the image capture plane (PCI) and said plane perpendicular to the horizontal axis (X'), and a line defined by the intersection between the reference plane (PREFD1, PREFG1) and said plane perpendicular to the horizontal axis (X'); and a second angle of inclination (AHD, AHG) of the image capture plane (PCI) relative to said first reference plane (PREFD1, PREFG1) in a plane perpendicular to an axis (Y) of said first reference plane (PREFD1, PREFG1) perpendicular to said horizontal axis (X'), which corresponds to the angle that exists in said plane perpendicular to said axis (Y) between a line defined by the intersection between the image capture plane (PCI) and said plane perpendicular to the axis (Y), and a line defined by the intersection between the reference plane (PREFD1, PREFG1) and said plane perpendicular to the axis (Y); and a computer adapted to respond to the signal representative of said at least one captured image to determine said refractive characteristic (D) of the individual's eyes (OD, OG) and to store in memory said at least one gaze direction parameter (H) associated with the gaze direction of the individual in association with the determined refractive characteristic.

\* \* \* \* \*

UNITED STATES PATENT AND TRADEMARK OFFICE
CERTIFICATE OF CORRECTION

PATENT NO. : 8,708,490 B2  Page 1 of 1
APPLICATION NO. : 13/508563
DATED : April 29, 2014
INVENTOR(S) : Konogan Baranton et al.

It is certified that error appears in the above-identified patent and that said Letters Patent is hereby corrected as shown below:

In the Specification

Column 10, line 1 should read:

--The corresponding images I1 and I2, as captured by the--

Column 10, line 37 should read:

--IROG1 of the reflection of the LED 21 in the image I1 is--

Column 10, line 39 should read:

--reflection of the LED 22 in the image I2. In other words,--

Signed and Sealed this
Twenty-fifth Day of November, 2014

Michelle K. Lee
*Deputy Director of the United States Patent and Trademark Office*